United States Patent [19]

Patel

[11] 4,049,408
[45] Sept. 20, 1977

[54] DISPOSABLE COLD PACK FOR BLOOD SPECIMEN

[75] Inventor: Harish A. Patel, Crystal Lake, Ill.

[73] Assignee: The Kendall Company, Boston, Mass.

[21] Appl. No.: 703,104

[22] Filed: July 6, 1976

Related U.S. Application Data

[63] Continuation-in-part of Ser. No. 556,721, March 10, 1975, abandoned.

[51] Int. Cl.² ............................................. F25D 5/02
[52] U.S. Cl. ...................................... 62/4; 128/403; 206/219
[58] Field of Search ............... 62/4; 206/219; 128/403

[56] References Cited

U.S. PATENT DOCUMENTS

| | | | |
|---|---|---|---|
| 2,907,173 | 10/1959 | Robbins | 206/219 |
| 3,175,558 | 3/1965 | Caillouette et al. | 128/403 |
| 3,887,346 | 6/1975 | Erdman | 62/4 |
| 3,893,834 | 7/1975 | Armstrong | 62/4 |

*Primary Examiner*—Frank W. Lutter
*Assistant Examiner*—Frank Sever

[57] ABSTRACT

A disposable cold pack for cooling and storing a sample of freshly drawn blood at 28° to 40° F. for 45 minutes has an outer flexible insulation layer and a pair of sealed flexible plastic envelopes. In one embodiment, the envelopes are arranged one within the other and the outer one secured to the insulation, the inner envelope being filled with water and frangible, the outer one containing ammonium nitrate in a ratio to water from 1.24:1 to 1.26:1 by weight, and a closure for securing the pack in folded position around the sample container. In another embodiment the envelopes are arranged side by side with a connecting passageway between them releasably sealed in closed condition.

11 Claims, 8 Drawing Figures

U.S. Patent  Sept. 20, 1977  Sheet 1 of 2  4,049,408
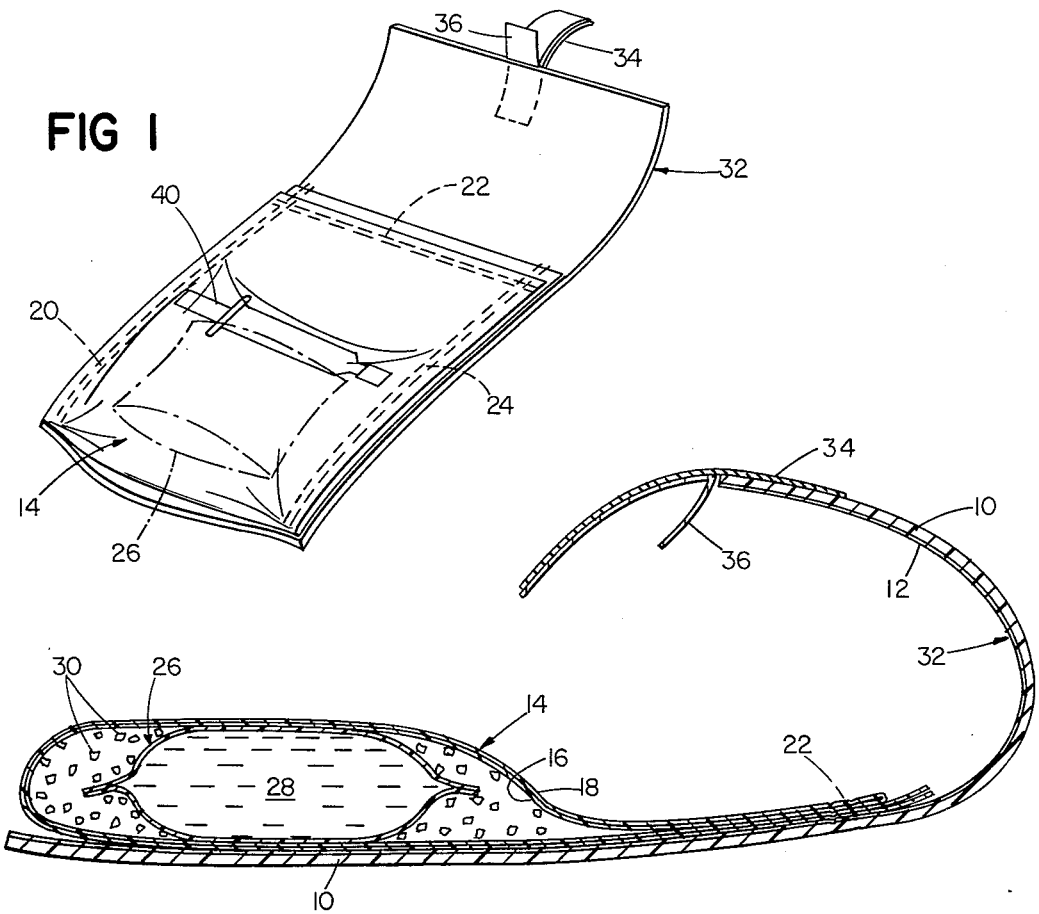
FIG 1
FIG 2
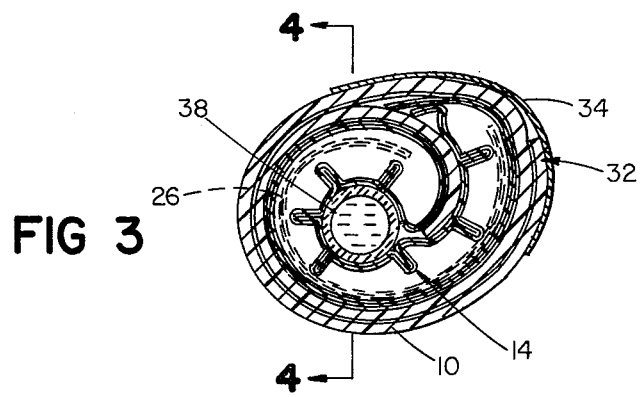
FIG 3
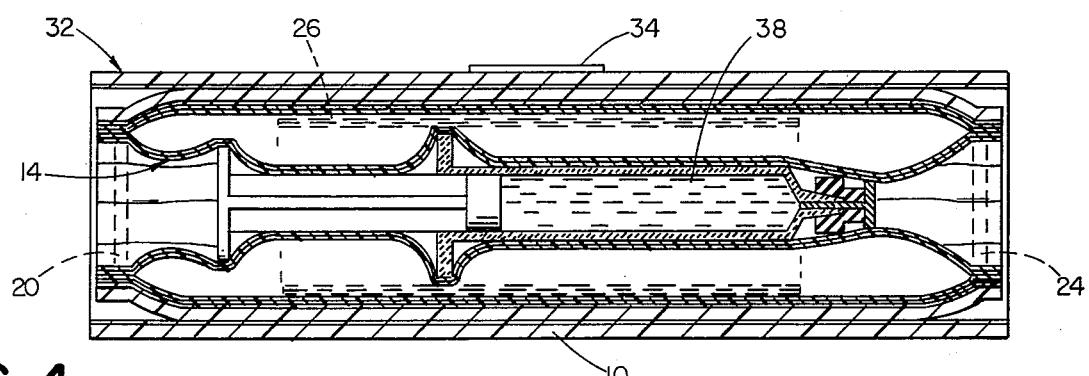
FIG 4

DISPOSABLE COLD PACK FOR BLOOD SPECIMEN

This application is a continuation in part of my co-pending application Ser. No. 556,721 filed Mar. 10, 1975, now abandoned This invention relates to a disposable cold pack for cooling and storing a container filled with a sample of freshly drawn blood for subsequent analysis.

In conducting certain analyses of samples of freshly drawn arterial blood, it is essential for optimum accuracy to carry out the analyses without delay, because when the sample is allowed to stand for more than a few minutes at room temperature, changes in composition occur which render the subsequent analysis inaccurate. It is frequently impossible to arrange for the necessary analytical equipment to be present at the location where the blood sample is drawn and so the practice has developed of immediately immersing the sample in its container, which is usually the sealed plastic or glass barrel of a syringe, in a bucket of ice or of a water-ice mixture in order to chill it as rapidly as possible and to maintain it at a temperature slightly above freezing while it is transported in the ice bucket to the analytical equipment. The elapsed time between the drawing of the sample and the beginning of analysis usually does not exceed 45 minutes. It is important that the temperature of the blood sample be maintained below 40° F. after it has been drawn because changes in composition occur fairly rapidly when the temperature of the blood sample exceeds that level. On the other hand, it is essential that the temperature of the sample not be reduced below 28° F. in order to avoid irreversible changes in cell structure caused by freezing. In the case of an ice bucket, tests have shown that a period of 7 minutes is required to lower the temperature of the usual 5 cc. blood sample from body temperature (99° F.) to 36° F. with crushed ice alone (no water), and 4 minutes with a water-ice mixture, in room temperature (76° F.) surroundings.

Although disposable cold packs such as the one described in Robbins et al. U.S. Pat. No. 2,925,719 have been available, they have failed to provide for chilling at maximum rate of speed without risk of cooling below the critical temperature of 28° F., while at the same time ensuring a temperature below 40° F. for a sufficiently long period of time. The present invention provides a disposable cold pack which can readily be activated without special equipment and which is effective to chill rapidly a container filled with a freshly drawn sample of blood from body temperature to a temperature within the range from 28° to 40° F. and to maintain it within that temperature range for at least 45 minutes. Tests have shown that preferred embodiments of the present invention are capable of cooling the usual 5 cc. blood sample from 99° to 36° F. within 2 minutes in room temperature (76° F.) surroundings. In one embodiment, the invention provides a disposable cold pack for cooling and storing a container filled with a sample of freshly drawn blood comprising an outer flexible insulation layer comprising foam plastic material, a first sealed flexible envelope of plastic material secured adjacent one face of the insulation layer, a supply of dry, solid ammonium nitrate disposed within the first envelope, a second sealed and frangible envelope containing a supply of water disposed within the first envelope and arranged to be broken by pressure applied externally to the first envelope to release the supply of water into the supply of ammonium nitrate within the first envelope to activate the cold pack, the weight ratio of ammonium nitrate to water being from 1.24:1 to 1.26:1 and a closure member having a pressure-sensitive adhesive face secured to the insulation layer for releasably maintaining the cold pack in folded position with the insulation layer outermost and with the sample container in contact with the first envelope, the cold pack being capable of chilling the blood sample rapidly and of maintaining it at a temperature of 28° to 40° F. for at least 45 minutes after activation in room temperature surroundings. In a preferred embodiment, the insulation layer includes a continuous film of flexible plastic bonded to the foam plastic material at the face adjacent the first envelope, and the first envelope is heat sealed along at least one marginal portion thereof to the insulation layer. In the preferred embodiment, the invention further features an insulation layer of rectangular configuration which is not only coextensive in area with one face of the rectangular first envelope but extends substantially beyond at least one margin of the first envelope to provide a flap, the closure member being secured to the margin of the flap remote from the first envelope. In the usual case where the size of the blood sample is approximately 5 cc., the total weight of water and ammonium nitrate must be from 180 to 200 grams for best results.

In other embodiments of the invention, the two envelopes are arranged side by side with a connecting passageway between them releasably sealed in closed condition.

Other features and advantages of the invention will appear from the drawing and from the detailed description which follows.

In the drawing:

FIG. 1 is an isometric view showing a one preferred embodiment of the invention before activation and use;

FIG. 2 is a view in cross-section on an enlarged scale showing the embodiment of FIG. 1 before activation and use;

FIG. 3 is a view in cross-section showing the device after activation with the sample container enfolded within it; and FIG. 4 is a view in cross-section taken along line 4—4 of FIG. 3.

Figure 5:
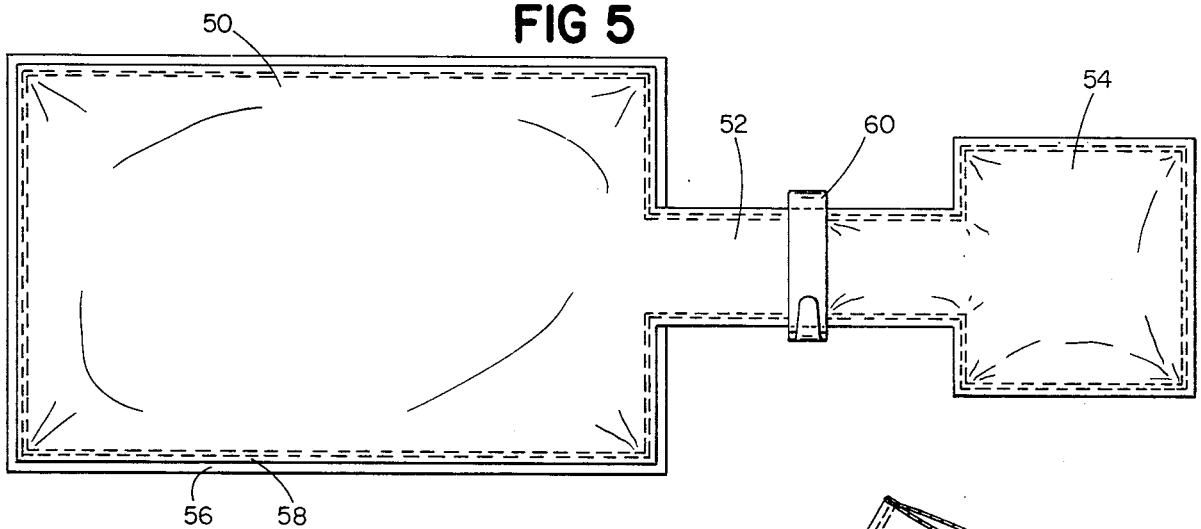
FIG. 5 is a plan view showing another emodiment of the invention before activation and use.

The embodiment shown in FIGS. 1-4 of the drawing includes an outer generally rectangular flexible insulation layer 10 of foam plastic material such as that sold under the trademark Microfoam approximately 1/16 inch thick laminated to an inner plastic film 12 of polyethylene approximately 2 mils thick, the two members 10 and 12 being coextensive in area and bonded together throughout their extent to serve as a laminated insulation layer. A sealed rectangular flexible envelope 14 formed of two sheets of 2 mil polyethylene film 16, 18 folded together is secured to film 12 and foam plastic layer 10 by heat sealing in zones 20, 22 and 24 along three margins of the rectangular envelope so that the face of the envelope 14 is adjacent the face of the insulating layer. Disposed within envelope 14 is a second sealed envelope 26 formed of a single layer of 2 mil polyethylene film or made up of composite layers of materials (inner layer of polyethylene laminated to slitted Mylar polyester film and outer layer of Mylar film coated with Saran polyvinylidene chloride) and filled with a supply 28 of water. The water-containing envelope 26, because of its relatively thin walls, is readily broken or ruptured by pressure applied externally of outer envelope 14 without breaking the walls of the outer envelope. Also disposed within outer envelope 14 is a supply 30 of dry solid ammonium nitrate in finely divided form. Preferably, air is evacuated from outer envelope 14 before heat sealing is completed so that the walls of the two envelopes will abut each other to facilitate rupturing of the inner envelope by external pressure. Envelope 14 extends over only a portion of the length of members 10 and 12 so that the latter extends beyond the heat sealed margin of envelope 14 to form a flap 32. To the margin of flap 32 remote from envelope 14 is secured as a closure member one or more lengths of pressure sensitive adhesive tape 34 provided with a removable temporary protective cover sheet 36 over its exposed adhesive face. Alternatively, a rubber band or piece of string, a band of cohesive (self-adherent) material or other mechanical fastening may be used in place of adhesive tape 34.

Although envelope 14 and insulation layer 10 are rectangular in configuration in the embodiment described above, it will be appreciated that other shapes such as oval may also be used. Indeed, it is possible, although less convenient, to have the insulation layer unattached to the outer envelope 14 but instead in the form of a separate flexible sheet together with a closure member; if desired, the separate insulation layer may be preformed into a cylindrical chamber or a box of appropriate dimensions.

In order to achieve the desired results, it is essential that the ratio of ammonium nitrate to water be from 1.24:1 to 1.26:1 by weight. In the case of a blood sample which is 5 cc. by volume, the size sample which is usually employed, the weight of ammonium nitrate and water should be from 180 to 200 grams for best results.

In using the cold pack, the barrel of the syringe into which the blood sample is drawn in the usual manner is released by inserting the end of the needle into a rubber stopper, or else the needle is first disconnected and discarded, after which the barrel is sealed. Inner envelope 26 is ruptured by manipulation of the cold pack so that the water is mixed with the ammonium nitrate, and barrel 38 of the syringe filled with the blood sample is then placed in the position indicated by printed design 40 on the face of envelope 14, and the envelope, together with the outer insulating layer, is folded upon itself to envelop the syringe barrel as shown in FIGS. 3 and 4. Temporary protective sheet 36 is stripped from the adhesive tape and the latter is pressed against the exposed face of insulation layer 10 as shown in FIGS. 3 and 4 to maintain the cold pack releasably in folded position snugly enveloping the syringe barrel 38. In the case where the insulating layer is separate from the envelope 14, it may be wrapped around the envelope simultaneously with envelopment of the syringe barrel 38 by the envelope or subsequently thereto, and secured in place by a closure member. In the case where the separate insulating layer is preformed into a container or box, the insulating layer can be rigid or stiff instead of flexible if desired and the container or box is of such size that the rolled up envelope 14 enclosing syringe barrel 38 is a snug fit within it, so that after insertion the envelope is maintained in rolledup condition around the syringe barrel.

In the embodiment shown in FIG. 5, envelope 50 is provided with a tube or side arm 52 connecting it to a second envelope 54, tube 52 providing communication between the two envelopes. In this embodiment the envelope 54 is substantially smaller than envelope 50 in overall dimensions and is supported solely by tube 52 which connects the two envelopes. Foam plastic layer 56 laminated to plastic film 58 is constructed and functions in the same way as layer 10 and film 12 of the embodiment of FIGS. 1-4. A spring metal or plastic clamp 60 releasably seals tube 52 in flattened condition, preventing communication between envelopes 50 and 54. Envelope 50 is filled with a supply of dry solid finely divided ammonium nitrate while envelope 54 is filled with water in the same amounts and proportions as envelopes 14 and 26 of the previous embodiment, with the difference that envelope 54 has walls of the same thickness as envelope 50 (which in turn has walls of the same thickness as envelope 14) and is not easily broken or ruptured.

Figure 6:
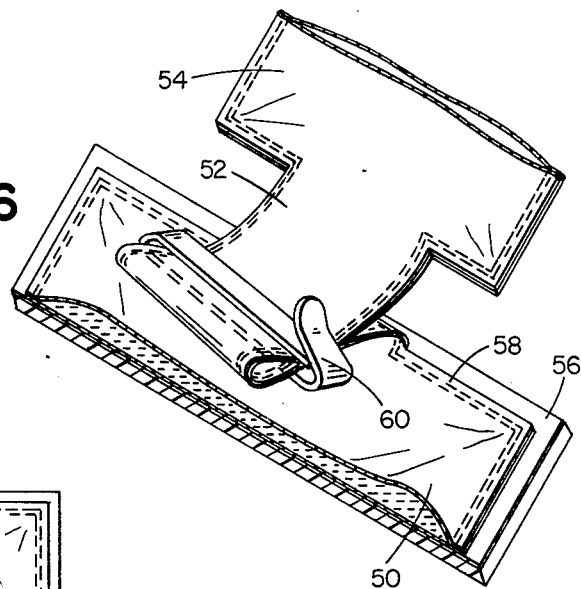
FIG. 6 is an isometric view, partly broken away and in section, showing the embodiment of FIG. 5 after activation.

In use of the embodiment shown in FIG. 5 to cool a syringe barrel full of blood the clamp 60 is released, the water is drained from envelope 54 into envelope 50, clamp 60 is reapplied as shown in FIG. 6 to the doubled over tube 52 to reseal it if desired, the syringe barrel is placed in position, and the assemblage is folded or wrapped upon itself. Any suitable means may be provided to hold the assemblage in folded or wrapped condition.

Figure 7:
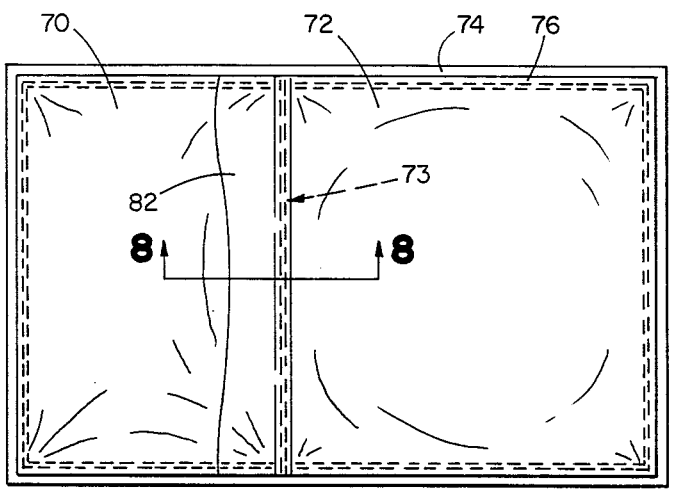
FIG. 7 is a plan view showing still another embodiment of the invention.
Figure 8:
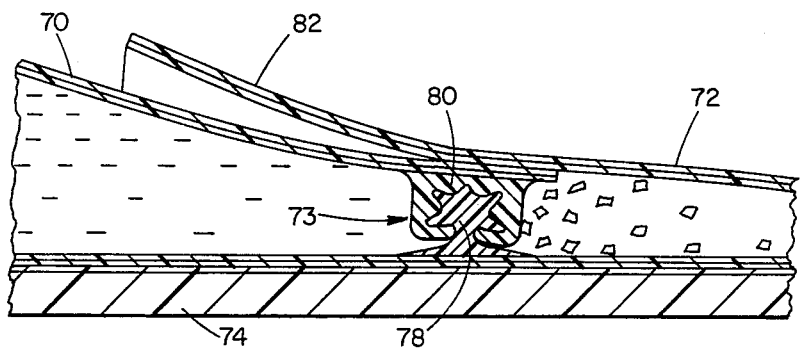
FIG. 8 is a view in section along line 8—8 of FIG. 7.

In the embodiment shown in FIG. 7, there are provided two side by side envelopes 70, 72 having common walls backed by a layer of foam plastic 74 and plastic film 76 coextensive with one side of both envelopes. In this embodiment the envelopes 70, 72 are of the same width, being formed by separating a single larger envelope into two portions by a transversely extending releasable seal 73. Envelope 70, which is substantially shorter, hence smaller in capacity than envelope 72, is thus in effect connected to envelope 72 by a tube of the same size as the periphery of the envelopes at their juncture. Releasable seal 73 between the two envelopes is provided in the form of a mating tongue and groove assembly including resilient tongue or post 78 of plastic material bonded along its length to the inner face of one wall of envelopes 70, 72 and a resilient groove 80 bonded along its length to the inner face of the opposing wall in position to receive tongue 78. Tongue 78 and groove 80 have mating cross sectional configurations so that when pressed together as shown in FIG. 8, they form a watertight seal. An extending flap 82 is provided at the outer face of the envelopes adjacent tongue 78 by cutting and overlapping the wall at this point, then heat sealing it in overlapped position as shown in FIG. 8; the flap is readily grasped by the fingers to facilitate separation or opening of the tongue and groove seal by pulling tongue 78 out of mating engagement with groove 80. Envelope 72 is filled with ammonium nitrate particles while envelope 70 is filled with water, tongue 78 being seated in groove 80 to maintain the components separate. The amounts and relative proportions of the components are the same as in the other embodiments. The device is used in the same manner as the other embodiments, being activated simply by pulling the tongue 78 out of engagement with groove 80 to permit the contents of the two envelopes to mix.

What is claimed is:

1. A disposable cold pack for cooling and storing a container filled with a sample of freshly drawn blood comprising
    a temperature regulation means which comprises the elements of a first sealed flexible envelope of plastic material,
    a supply of dry solid ammonium nitrate disposed within said first envelope,
    a second sealed and frangible envelope containing a supply of water disposed within said first envelope and arranged to be broken by pressure applied externally to said first envelope to release said supply of water into said supply of ammonium nitrate within said first sealed envelope to activate said cold pack,
    the weight ratio of ammonium nitrate to water being from 1.24:1 to 1.26:1, the total weight of ammonium nitrate and water being from 180 to 200 grams, the elements of said temperature regulating means cooperatively functioning, upon the breaking of said second envelope, to cool said sample to a temperature low enough to avoid composition changes therein, but high enough to avoid freezing thereof, for a period of at least 45 minutes.
    said cold pack being adapted to be folded around said sample container with the container in contact with said first envelope.

2. A cold pack as claimed in claim 1 comprising in addition an outer layer of insulation engaging the outer face of said first envelope.

3. A cold pack as claimed in claim 2 in which said layer of insulation comprises a layer of flexible foam plastic material secured adjacent the face of said first envelope, and in which a closure member is secured to said insulation layer for releasably maintaining said cold pack in folded position with said insulation layer outermost.

4. A cold pack as claimed in claim 3 in which said insulation layer includes a continuous film of flexible plastic bonded to said foam plastic material at the face adjacent said first envelope, and said first envelope is heat sealed along at least one marginal portion thereof to said insulation layer.

5. A cold pack as claimed in claim 4 in which said insulation layer extends fully across the adjacent first envelope and extends substantially beyond at least one margin of said first envelope to provide a flap, and said closure member is secured to the margin of said flap remote from said first envelope.

6. A cold pack as claimed in claim 5 in which said inner envelope is formed of a single layer of polyethylene film and said outer envelope is formed of a double layer of said film, is of rectangular configuration, and is heat sealed along three margins to said insulation layer.

7. A cold pack as claimed in claim 5 in which said closure member has a pressure-sensitive adhesive face for releasably holding the margin of said flap against the outer face of said insulation layer.

8. A cold pack as claimed in claim 1, in which said temperature regulation means functions to cool said sample to a temperature of 28°–40° F for a period of at least 45 minutes.

9. A disposable cold pack for cooling and storing a container filled with a sample of freshly drawn blood comprising
    A. a temperature regulation means which comprises the elements of a single sealed flexible outer envelope of plastic material,
    B. an outer insulating layer of flexible foam plastic material engaging the outer face of said outer envelopes and secured thereto, said insulating layer extending fully across the face of said first envelope and substantially beyond at least one margin of said envelope to form a flexible flap,
    C. a supply of dry solid ammonium nitrate disposed within said outer envelope,
    D. an inner sealed and frangible envelope containing a supply of water disposed within said outer envelope and arranged to be broken by pressure applied externally to said outer envelope to release said supply of water into said supply of ammonium nitrate within said outer sealed envelope to activate said cold pack,
    the weight ratio of ammonium nitrate to water being from 1.24:1 to 1.26:1 and the total weight of ammonium nitrate and water being from 180 to 200 grams,
    a closure member secured to said insulation layer flap at the margin thereof remote from said outer envelope for releasably maintaining said cold pack in folded position with said insulation layer outermost extending completely around the outer circumference of said folded cold pack,
    said cold pack being adapted to be folded around said sample container with the container in contact with said outer envelope for the elements of said temperature regulation means cooperatively functioning to chill said blood sample rapidly and to maintain it at a temperature of 28° to 40° F. for at least 45 minutes after activation in room temperature surroundings.

10. A disposable cold pack for cooling and storing a container filled with a sample of freshly drawn blood comprising
    a first sealed flexible envelope of plastic material,
    an outer insulating layer of flexible foam plastic material engaging the outer face of said outer envelope and secured thereto, said insulating layer extending fully across the face of said first envelope,
    A. temperature regulation means comprising the elements of a supply of dry solid ammonium nitrate disposed within said first envelope,
    B. a second sealed flexible envelope of plastic material disposed outside of and adjacent the first,
    C. a supply of water disposed within said second envelope,
    the weight ratio of ammonium nitrate to water being from 1.24:1 to 1.26:1 and the total weight of ammonium nitrate and water being from 180 to 200 grams,
    D. means connecting said first and second envelopes to permit mixing of the contents of the two envelopes, said elements of said temperature regulation means cooperatively functioning, upon said mixing, to chill said sample to a temperature low enough to avoid composition changes therein, but high enough to avoid freezing thereof, for a period of at least 45 minutes, and
    means for releasably sealing said connecting means to maintain the contents of the two envelopes separate.

11. A cold pack as claimed in claim 9, in which said temperature regulation means functions to cool said sample to a temperature of 28°–40° F for a period of at least 45 minutes.

* * * * *

UNITED STATES PATENT AND TRADEMARK OFFICE
CERTIFICATE OF CORRECTION

PATENT NO. : 4,049,408
DATED : September 20, 1977
INVENTOR(S) : Harish A. Patel

It is certified that error appears in the above-identified patent and that said Letters Patent are hereby corrected as shown below:

Column 3, line 45, "released" should be --sealed--;

Column 4, line 2, "rolledup" should be --rolled-up--;

Column 5, line 26, delete the period after "minutes" and insert a comma;

Column 6, line 6, "envelopes" should be --envelope--.

Signed and Sealed this

Twentieth Day of December 1977

[SEAL]

Attest:

RUTH C. MASON
Attesting Officer

LUTRELLE F. PARKER
Acting Commissioner of Patents and Trademarks